United States Patent
Otsubo

(10) Patent No.: US 7,112,193 B2
(45) Date of Patent: Sep. 26, 2006

(54) DISPOSABLE DIAPER BACKSHEET COMPRISING COMPOSITE HAVING AN ELASTIC LAYER, INELASTIC LAYER AND BONDING PATTERN OF OBLIQUELY INTERSECTING LINES

(75) Inventor: Toshifumi Otsubo, Ehime-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 478 days.

(21) Appl. No.: 10/206,190

(22) Filed: Jul. 29, 2002

(65) Prior Publication Data

US 2002/0193774 A1     Dec. 19, 2002

Related U.S. Application Data

(63) Continuation-in-part of application No. 08/937,515, filed on Sep. 25, 1997, now abandoned.

(30) Foreign Application Priority Data

Sep. 30, 1996   (JP)   ................................. 8-259571

(51) Int. Cl.
*A61F 13/514*   (2006.01)
*A61F 13/51*    (2006.01)
*A61F 13/496*   (2006.01)

(52) U.S. Cl. .................... 604/385.22; 604/385.29; 604/385.3; 604/385.24; 604/385.25

(58) Field of Classification Search ........ 604/358–402; 428/198, 101; D24/126
See application file for complete search history.

(56) References Cited

U.S. PATENT DOCUMENTS

| 2,627,858 A | 2/1953 | Miller |
| 3,236,238 A | 2/1966 | Morse |
| 3,561,447 A * | 2/1971 | Alexander .................. 604/364 |
| 3,695,985 A * | 10/1972 | Brock et al. ................ 428/152 |
| 4,333,979 A | 6/1982 | Sciaraffa et al. |
| 4,397,645 A | 8/1983 | Buell |
| 4,418,123 A | 11/1983 | Bonnelle et al. |

(Continued)

FOREIGN PATENT DOCUMENTS

EP    0 604 731    7/1994

(Continued)

OTHER PUBLICATIONS

Printout of Efunda.com conversion of 1.5 mils to various equivalent lengths, accessed Dec. 9, 2005.*

*Primary Examiner*—Tatyana Zalukaeva
*Assistant Examiner*—Keshia Gibson
(74) *Attorney, Agent, or Firm*—Lowe Hauptman & Berner LLP

(57) ABSTRACT

A disposable diaper includes a backsheet comprising an elastic inner layer and an inelastic outer layer. The elastic inner layer, in a transversely stretched state, is joined to the inelastic outer layer at a plurality of intermittently disposed spots. The spots are lined up to form a series of imaginary lines disposed on a bias between the longitudinal and transverse directions of the disposable diaper. In each of areas between the spots, defined by a plurality of intersecting imaginary lines that pass through a plurality of the spots that are closely arranged in succession, the inelastic outer layer is free to separate from the elastic inner layer upon contraction (relaxation) of the elastic inner layer, and thereupon the outer layer forms a plurality of longitudinal pleats. The pleats, formed by relaxing the transversely stretched inner layer, are disposed in a direction that is substantially normal to the direction of stretching.

33 Claims, 3 Drawing Sheets

U.S. PATENT DOCUMENTS

| | | | |
|---|---|---|---|
| 4,515,595 A | 5/1985 | Kieuit et al. | |
| 4,639,949 A | 2/1987 | Ales et al. | |
| 4,642,819 A | 2/1987 | Ales et al. | |
| 4,681,580 A | 7/1987 | Reising et al. | |
| 4,720,415 A | 1/1988 | Vander Wielen et al. | |
| 4,747,846 A | 5/1988 | Boland et al. | |
| 4,808,252 A | 2/1989 | Lash | |
| 4,842,596 A | 6/1989 | Kielpikowski et al. | |
| 4,844,965 A | 7/1989 | Foxman | |
| 4,847,134 A | 7/1989 | Fahrenkrug et al. | |
| 4,891,258 A | 1/1990 | Fahrenkrug et al. | |
| 5,114,781 A * | 5/1992 | Morman | 428/198 |
| 5,171,239 A | 12/1992 | Igave et al. | |
| 5,221,270 A | 6/1993 | Buell et al. | |
| 5,330,817 A * | 7/1994 | Arnott et al. | 428/85 |
| 5,340,424 A * | 8/1994 | Matsushita | 156/164 |
| 5,399,174 A | 3/1995 | Yeo et al. | |
| 5,451,219 A | 9/1995 | Suzuki et al. | |
| 5,543,206 A * | 8/1996 | Austin et al. | 428/198 |
| 5,576,090 A | 11/1996 | Suzuki | |
| 5,613,960 A | 3/1997 | Mizutani | |
| 5,681,302 A | 10/1997 | Melbye et al. | |
| 5,837,352 A | 11/1998 | English et al. | |
| 6,093,665 A | 7/2000 | Sayouitz et al. | |

FOREIGN PATENT DOCUMENTS

| | | |
|---|---|---|
| JP | 3-122824 | 12/1991 |
| WO | WO99/16400 | 4/1999 |

* cited by examiner

DISPOSABLE DIAPER BACKSHEET COMPRISING COMPOSITE HAVING AN ELASTIC LAYER, INELASTIC LAYER AND BONDING PATTERN OF OBLIQUELY INTERSECTING LINES

RELATED APPLICATION

The present application is a continuation-in-part of application Ser. No. 08/937,515, filed Sep. 25, 1997 now abandoned, entitled "DISPOSABLE DIAPER".

BACKGROUND THE INVENTION

This invention relates to a disposable diaper and more particularly to such a diaper having a plurality of pleats formed by a backsheet thereof.

It is well known in the art of disposable diapers to make a backsheet thereof from an inner layer of plastic film and an outer layer of nonwoven fabric in order to improve a touch of the diaper. For example, Japanese Laid-Open Utility Model Application No. Hei 3-122824 discloses a disposable diaper comprising a backsheet consisting of an elastic outer layer of plastic film or rubber film and an elastic inner layer of non woven fabric intermittently joined to each other so that these layers may be in the form of a single member that is elastic for stretch and contraction.

However, the woven fabric, in the form of the elastic inner layer constituent of the known backsheet, may often lose the softness that is peculiar to nonwoven fabrics once it has been joined to the plastic film elastic outer layer that is another constituent of the backsheet. Consequently, the soft touch required for the diaper is apt to be deteriorated in comparison with the case in which the nonwoven fabric is used alone for the backsheet. Such known backsheet is disadvantageous also from an economical viewpoint, since the elastic nonwoven fabric and film are generally more expensive than those that are inelastic.

SUMMARY OF THE INVENTION

In view of the problems as have been described above, it is a principal object of the invention to provide a disposable diaper having a backsheet having desired softness as well as elasticity and being obtainable at a relatively low cost.

The object set forth above is achieved, according to the invention, by a disposable diaper having a front waist region, a rear waist region and a crotch region therebetween, said diaper comprising a liquid-permeable topsheet, a liquid-impermeable backsheet and a liquid-absorbent core disposed therebetween; wherein said backsheet, in at least said front waist region, comprises and elastic inner layer and an inelastic outer layer that is overlapped with said elastic inner layer; and said elastic inner layer and said inelastic outer layer are joined to each other at a plurality of intermittently arranged spots. The inner and outer layer are spot joined together when said elastic inner layer is in a condition of being stretched transversely of said diaper so that, in areas disposed between imaginary intersecting lines that each pass through and are described by a plurality of said spots that are closely arranged in succession, said inelastic outer layer is free to separate from said elastic inner layer and, upon relaxation of stretching of the inner elastic layer, form a plurality of pleats.

The disposable diaper according to the invention is characterized by the backsheet that comprises, at least in the front waist region, the described elastic inner layer and the inelastic outer layer. The inelastic outer layer separates from the elastic inner layer as the latter is contracted so as to form a plurality of pleats that are convex away from the inner layer, that is outward. Such pleats formed in the inelastic outer layer effectively provide the diaper with the comfortable soft touch that is peculiar to a nonwoven fabric.

Other and further objects, features and advantages of the invention will appear more fully from the following description.

DESCRIPTION OF THE PREFERRED EMBODIMENT

Figure 1:
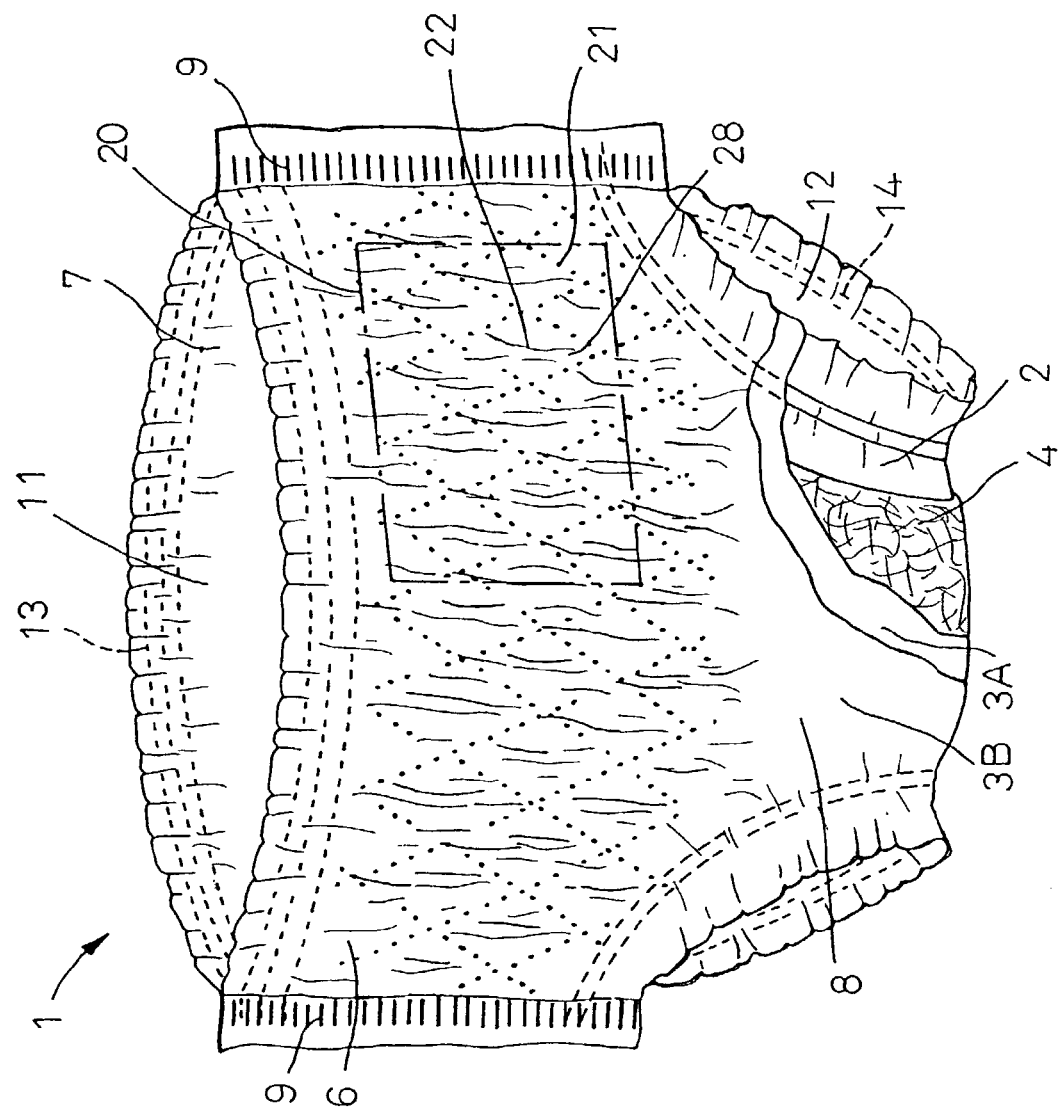
FIG. 1 is a perspective view showing an embodiment of the disposable diaper according to the invention with portions partially broken away.

FIG. 1 shows a pull-on or pants type diaper 1 in a perspective view with a portion broken away. The diaper 1 is shown in FIG. 1 as contracted transversely. The diaper 1 comprises a liquid-permeable topsheet 2 intended to contact the wearer's skin, a backsheet 3 and a liquid-absorbent core 4 disposed between these two sheets 2, 3. The topsheet 2 and the backsheet 3 are over laid, with the core 4 therebetween, and bonded to each other by means of hot melt adhesive (not shown) over their portions extending outward beyond a peripheral edge of the absorbent core 4 by which a laminated is formed. This laminate defines a front waist region 6, a rear waist region 7 and a crotch region 8 entering between these two waist regions 6, 7. The front and rear waist regions 6, 7 are put flat and joined together at a plurality of intermittent spots arranged in the longitudinal direction of the diaper along their transversely opposite side edges 9 so as to define a waist-opening 11 and a pair of leg-openings 12. These openings 11, 12 are provided with circumferentially extending elastic members 13 and 14, respectively, that are disposed between the topsheet 2 and the backsheet 3. These elastic members 13, 14 are secured under appropriate tension to inner surface(s) of the topsheet 2 and/or the backsheet 3, the backsheet 3 consists of an elastic inner layer 3A, that is stretchable and contractible, and an inelastic outer layer 3B. Of the front and rear waist regions 6, 7 and the crotch region 8, at least the front waist region 6 has a plurality of spots 21 at which the elastic inner layer 3A and the inelastic outer layer are joined to each other and a plurality of pleats 22 extending longitudinally of the diaper 1.

Figure 2:
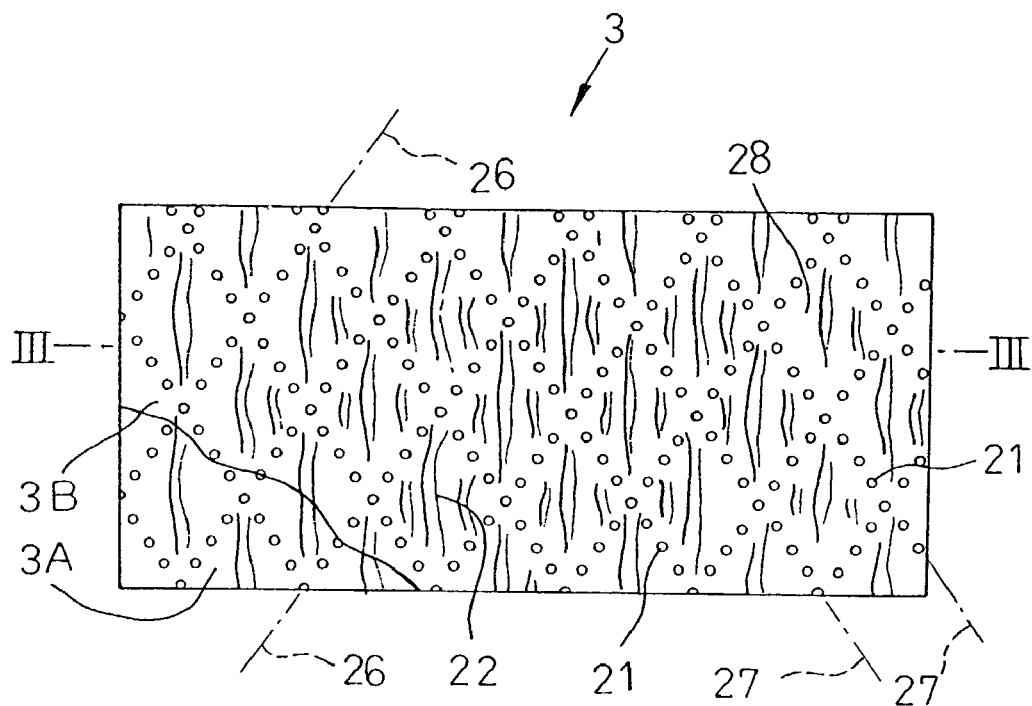
FIG. 2 is a diagram showing a part of a backsheet of the diaper.
Figure 3:
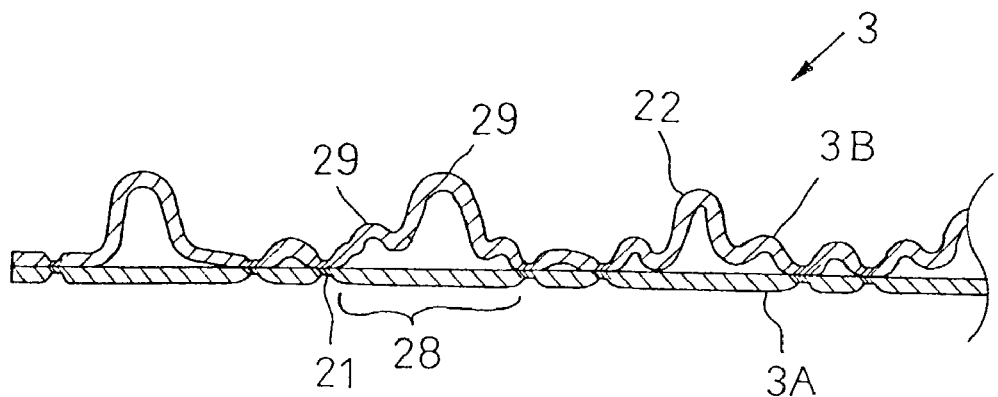
FIG. 3 is a sectional view taken along a line III—III in FIG. 2.

FIG. 2 is a fragmentary plan view showing a portion of the backsheet 3 enclosed by an imaginary line 20 that is shown in FIG. 1; and FIG. 3 is a sectional view taken along a line III—III in FIG. 2. The elastic inner layer 3A is made of at least transversely stretchable and contractible material such as elastomer film of thermoplastic synthetic resin or rubber. FIGS. 2 and 3 show the elastic inner layer 3A in its relaxed, contracted state. The inelastic outer layer 3B is made of substantially unstretchable and uncontractible fibrous material, such as inelastic spun bond non woven fabric containing thermoplastic synthetic fibers, and has a plurality of pleats 22 extending substantially in the longitudinal direction of the diaper 1. The elastic inner layer 3A and the inelastic outer layer 3B are joined together at the spots 21 at which a portion of synthetic resin contained in at least one of these layer 3A, 3B is molten and then solidified. The spots 21 are arranged closely along imaginary lines extending in predetermined directions. Referring to FIG. 2, the spots 21 are arranged along a plurality of substantially parallel imaginary lines 26 ascending obliquely to the right ascending and a plurality of substantially parallel imaginary lines 27 descending obliquely to the right. Each pair of adjacent lines 26 and each pair of adjacent lines 27 cross each other to produce each defined area in the depicted shape of a lozenge 28. In each of the areas 28, upon relaxation and contraction of the elastic layer 3A, portions of the inelastic outer layer 3B separate from the elastic inner layer 3A and thereby form the previously mentioned pleats 22. Both the configuration and the number of the pleats 22 are indeterminate. The pleats 22 may have one or more crest (s) 29 within each of the areas 28, as seen in FIG. 3 showing the pleats 22 in a sectional view.

Figure 4:
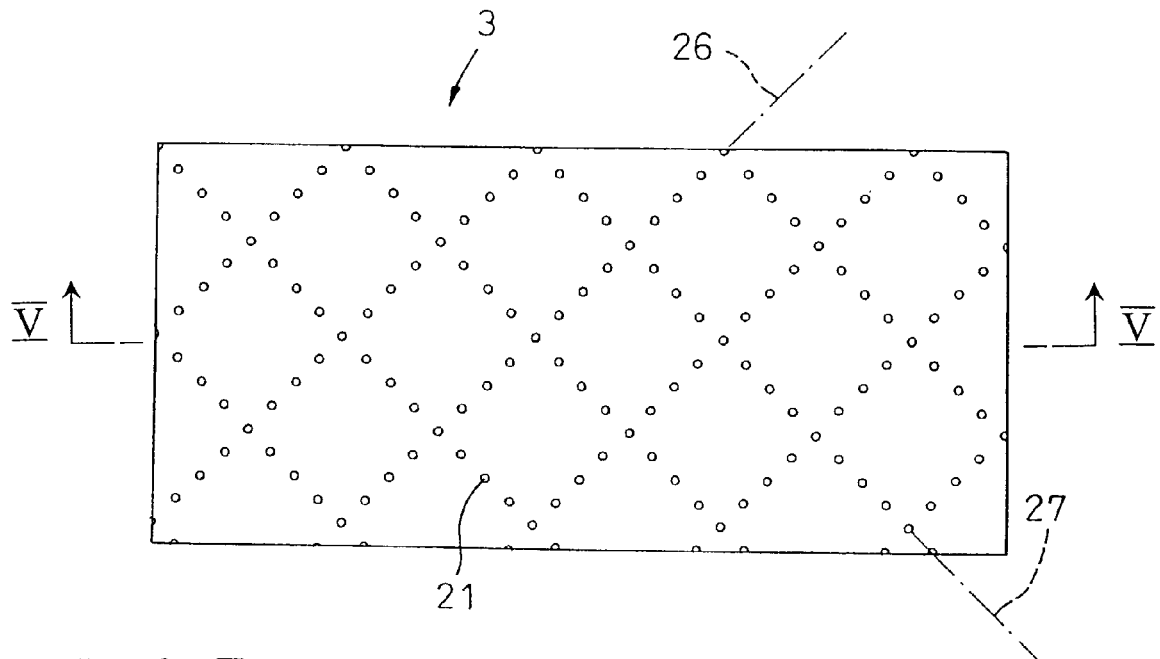
FIG. 4 is a fragmentary plan view showing the backsheet in its stretched state.
Figure 5:
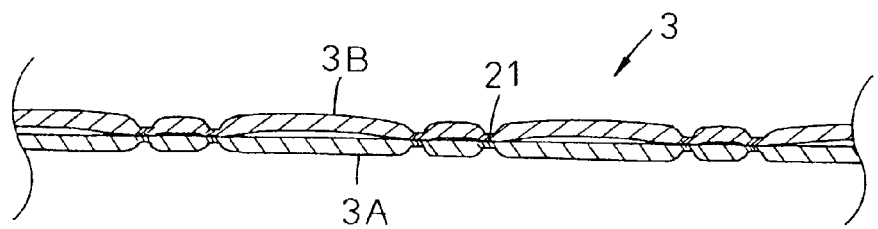
FIG. 5 is a fragmentary sectional view taken along the line V—V on FIG. 4 looking in the direction of the arrows and showing the backsheet as being in its stretched state.

FIGS. 4 and 5 show the backsheet 3 being transversely stretched in a plan view and in a sectional view, respectively. The backsheet 3 is stretched as the elastic inner layer 3A is elastically stretched until the pleats 22 of the inelastic outer layer 3B are completely unfolded. Thereupon, the backsheet 3 becomes substantially flat as shown and the diaper 1 itself shown in FIG. 1 is transversely expanded to also become flat. Referring to FIG. 4, the imaginary lines 26, 27 passing through the spots 21 i.e., the lines 26, 27 along which the spots 21 are arranged, are inclined at angle of approximately 45 degree with respect to the transverse direction. The illustrated embodiment of the backsheet 3 may be obtained in a manner as illustrated by FIGS. 4 and 5. Specifically, an original web of the inner layer 3A, which is elastic for stretch and contraction, is stretched to a predetermined elongation percentage. Then, an original web of the inelastic layer 3B is placed upon the stretched web of the inner layer 3A. The original webs of these layers 3A, 3B thus placed one upon another are fed between a pair of thermally embossing rolls to obtain a laminated sheet joined at the spots in a predetermined pattern. The backsheet 3 may be cut out from this laminated sheet. The contraction of the elastic inner layer 3A causes the pleats 22 to be formed in a direction that is orthogonal to the direction in which the elastic inner layer 3A is contracted. It should be understood that the pattern of the pleats depends on the pattern of the spots 21.

With the diaper 1, having a backsheet 3 constructed as has been described above, a comfortable soft touch, peculiar to the nonwoven fabric, can be maintained in spite of the laminate structure of the backsheet 3 with the plastic or rubber film. That is because portions the inelastic outer layer 3B separate from the elastic inner layer 3A in each of the areas 28 so as to form the pleats 22.

Figure 6:
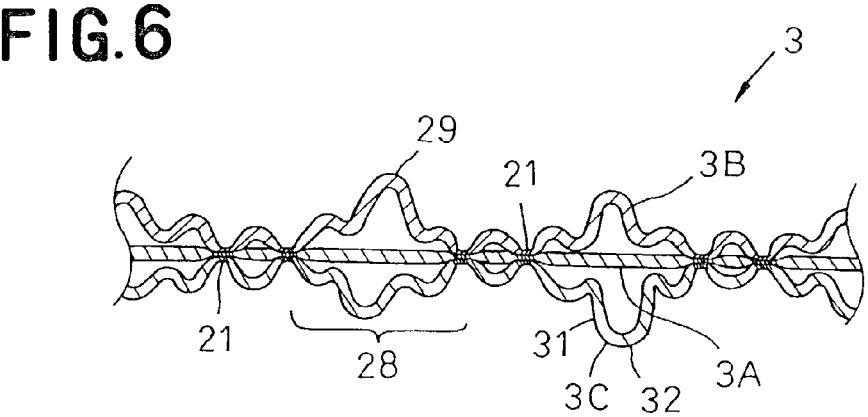
FIG. 6 is a view similar to FIG. 3 showing a variant of the backsheet.

FIG. 6 is a sectional view similar to FIG. 3 showing a variant of the backsheet 3 used for the invention. This embodiment of the backsheet 3 comprises, in addition to the elastic inner layer 3A and the inelastic outer layer 3B, an inelastic third layer 3C. The inelastic third layer 3C is made of material similar to the fibrous material of the inelastic outer layer 3B, for example of spun bond nonwoven fabric containing thermoplastic synthetic fibers. The inelastic third layer 3C is joined to the elastic inner layer 3A at the spots 21 at which the inner and outer layers 3A, 3B are also joined to each other at spots 21. In each of the areas 28, the inelastic third layer 3C separates from the elastic inner layer 3A in a direction opposite to the inelastic outer layer (downward as viewed in FIG. 6) so as to form pleats 31 having crests 32. An apparent thickness corresponding to the distance between the crests 29, 32 presented by the backsheet 3 of such structure in its contracted state is substantially larger than the thickness presented by the backsheet 3 in its stretched state. Such contracted backsheet 3 is comfortably soft and has a large cushioning effect.

To implement the invention, the elastic inner layer 3A, forming a constituent of the backsheet 3, is preferably made of elastic film having an elastic recovery of 60–100%, after having been stretched by 30–100%, and a thickness of 0.01–0.1 mm. The elastic film preferably used has an elastically deformable tension. The inelastic outer layer 3B and the inelastic third layer 3C are preferably made of nonwoven fabric having a bulk density of 15–200 g/m$^2$. The size and pattern of the spots 21 may be selected so that they do not substantially affect the elasticity of the elastic inner layer 3A and can cause the pleats 22 to form, whereby providing the diaper 1 with a desired softness. This is achieved, for example, by the spots 21 each having an area of 0.7–9 mm$^2$ and being spaced apart from an adjacent spot 21 by 1–5 mm. The imaginary lines 26, 27 described by the spots 21, and are successively adjacent one to another, may be either straight or curved. In the case of the embodiment shown by FIG. 4, the spots 21, are each defined by a circle having a diameter of approximately 1.8 mm, are spaced apart one from by a center-to-center distance of approximately 4 mm so as to form the imaginary straight lines 26, 27, respectively. Each pair of adjacent imaginary straight lines 26 and each pair of imaginary adjacent straight lines 27 are both spaced apart in parallel with each other by approximately 20 mm, respectively. The spots at which the inelastic outer layer 3B and the inelastic third layer 3C are joined to the elastic inner layer 3A, respectively, may be separately provided instead of providing them commonly as shown in FIG. 6. Concerning the elastic inner layer 3A, it is not essential for the elastic inner layer 3A to cover the diaper 1 entirely. It is also possible to provide it on a part of the diaper 1, for example along transversely opposite side edges of the front waist region 6 and/or the rear 7, so as to form the pleats 22 in only these regions of the diaper 1.

The entire disclosure of Japanese Patent Application No. Hei 8-259571 filed on Sep. 30, 1996 including specification, claims, drawings and abstract are incorporated herein by reference in its entirety.

Having described our invention as related to the embodiments shown in the accompanying drawings, it is our intention that the invention be not limited by any of the details of description, unless other wise specified, but rather be construed broadly within its spirit and scope as set out in the accompanying claims.

What is claimed is:

1. A disposable diaper having a front waist region, a rear waist region and a crotch region therebetween, said diaper further comprising a liquid-permeable top sheet, a liquid-impermeable back sheet and a liquid-absorbent core disposed therebetween, said diaper having a longitudinal direction from said front waist region to said rear waist region, and a transverse direction that is substantially normal to said longitudinal direction;

wherein:
  said back sheet, in at least said front waist region, comprises an elastic inner layer extending throughout an entire front panel and an inelastic outer layer overlapped with said elastic inner layer;

said elastic inner layer and said inelastic outer layer are joined to each other at a plurality of intermittently arranged spots, wherein said spots are arranged to form imaginary lines that are obliquely disposed with respect to said transverse direction;

said imaginary lines intersect with each other to form a series of closed figures and each side of said closed figures includes more than two of said spots;

said inner and outer layers have been joined to each other at said spots when said elastic inner layer was in a transversely stretched condition so that, when said stretched inner layer is relaxed and thereby contracted transversely of said diaper, said outer layer forms a plurality of substantially longitudinal pleats;

said inner and outer layers are not directly joined to each other within a perimeter of any of said closed figures;

said diaper further comprises at least one circumferentially extending elastic member extending along a waist opening defined by longitudinally opposite edges of said front and rear waist regions, respectively, when the diaper is being worn by a wearer; and all of said spots are longitudinally spaced from said circumferentially extending elastic member.

2. The diaper of claim 1, further comprising an inelastic third layer made of inelastic fibrous material, wherein said inelastic third layer is joined to said elastic inner layer at a plurality of intermittently arranged spots, which are arranged to form a plurality of imaginary lines that are obliquely disposed with respect to said longitudinal and transverse directions, when said inner layer is stretched so that, upon relaxation of said stretching and thereby contraction of said elastic inner layer, said inelastic third layer forms a plurality of substantially longitudinal pleats.

3. The diaper of claim 2, wherein at least one of said elastic inner layer, said inelastic outer layer and said inelastic third layer contains thermally meltable synthetic resin and said spots, at which said elastic inner layer and said inelastic outer and inelastic third layers are joined one to another, include melted and solidified said resin.

4. The diaper of claim 2, wherein
said inelastic outer layer is joined to an outer surface of said elastic inner layer and said third inelastic layer is joined to an inner surface of said elastic inner layer at common said spots.

5. The diaper of claim 2, wherein said elastic inner layer comprises at least transversely stretchable and contractible material and said inelastic outer and third layers comprise substantially uncontractible fibrous materials, respectively.

6. The diaper of claim 2, wherein said elastic inner layer is plastic or rubber film and said inelastic outer and third layers are nonwoven fabrics.

7. The diaper of claim 2, wherein
the inelastic outer layer and the inelastic third layer are made of nonwoven fabric having a bulk density of from 15 to 200 g/m$^2$.

8. The diaper of claim 1, wherein at least one of said elastic inner layer and said inelastic outer layer contains thermally meltable synthetic resin and said spots, at which said elastic inner layer and said inelastic outer layer are joined to each other, include melted and solidified said resin.

9. The diaper of claim 1 wherein said imaginary lines comprise a first set of non-intersecting imaginary lines which are generally disposed in a first direction, and a second set of non-intersecting imaginary lines which are generally disposed in a second direction crossing said first direction.

10. The diaper of claim 9, wherein substantially all of said imaginary lines are disposed in either said first set or said second set.

11. The diaper of claim 9, wherein the imaginary lines forming each of said closed figures include a first pair of parallel said imaginary lines belonging to the first set and extending in the first direction, and a second pair of parallel said imaginary lines belonging to the second set and extending in the second direction.

12. The diaper of claim 11, wherein said first and second pairs extend obliquely relative to the longitudinal direction of the diaper.

13. The diaper of claim 9, wherein each of sold spots has an area of from 0.7 to 9 mm$^2$, and two adjacent said spots on the same imaginary Line are spaced by a center-to-center distance of from 1 to 5 mm.

14. The diaper of claim 13, wherein each of said spots has a diameter of 1.8 mm, and two adjacent said spots on the same imaginary line are spaced by a center-to-center distance of 4 mm.

15. The diaper of claim 13, wherein the imaginary lines in each of the first and second sets are substantially straight and parallel, and two adjacent parallel said imaginary lines are spaced from each other by approximately 20 mm.

16. The diaper of claim 9, wherein a spacing between adjacent said spots arranged on the same imaginary line is smaller than a spacing between adjacent said non-intersecting imaginary lines of the first or second set.

17. The diaper of claim 9, wherein, when said elastic inner layer is transversely stretched, said first set of said imaginary lines crosses said second set of said imaginary lines at about right angles.

18. The diaper claim 1, when said elastic inner layer is transversely stretched, said first set of said imaginary lines crosses said second set of said imaginary lines at about right angles.

19. The diaper of claim 1, wherein each closed figure is a parallelogram.

20. The diaper of claim 1, wherein
each closed figure is lozenge shaped.

21. The diaper of claim 1, wherein each of said imaginary lines intersects with at least one other of said imaginary lines.

22. The diaper of claim 1, wherein
each side of said closed figures includes at least five of said spots.

23. The diaper of claim 1, wherein the inelastic outer layer is made of substantially uncontractible fibrous material.

24. The diaper of claim 23, wherein the inelastic outer layer is made of inelastic spun bond non woven fabric containing thermoplastic synthetic fibers.

25. The diaper of claim 1, wherein the elastic inner layer is made of an elastic film having an elastic recovery of from 60 to 100%, after having been stretched by from 30 to 100%, and a thickness of from 0.01 to 0.1 mm.

26. The diaper of claim 1, wherein
said back sheet in at least said front panel, is double-layer structure consisting of said elastic inner layer and said inelastic outer layer only.

27. The diaper of claim 1, wherein said elastic inner layer is distinct and separate from said circumferentially extending elastic member.

28. The diaper of claim 1, wherein said front panel extends from the front waist region down to a region that is coelevational with an upper end of leg openings formed in the diaper.

29. A disposable diaper having a front waist region, a rear waist region and a crotch region therebetween, said diaper further comprising a liquid-permeable top sheet, a liquid-impermeable back sheet and a liquid-absorbent core disposed therebetween, said diaper having a longitudinal direction from said front waist region to said rear waist region, and a transverse direction that is substantially normal to said longitudinal direction;

wherein:

said back sheet, in at least said front waist region, comprises an elastic inner layer extending throughout an entire front panel and an inelastic outer layer overlapped with said elastic inner layer;

said elastic inner layer and said inelastic outer layer are joined to each other at a plurality of intermittently arranged spots, wherein said spots are arranged to form imaginary lines that are obliquely disposed with respect to said transverse direction;

said imaginary lines intersect with each other to form a series of closed figures and each side of said closed figures includes plural said spots;

said inner and outer layers have been joined to each other at said spots when said elastic inner layer was in a transversely stretched condition so that, when said stretched inner layer is relaxed and thereby contracted transversely of said diaper, said outer layer forms a plurality of substantially longitudinal pleats;

said inner and outer layers are not directly joined to each other within a perimeter of any of said closed figures;

said front panel extends from the front waist region down to a region that is coelevational with an upper end of leg openings formed in the diaper;

said diaper further comprises at least one circumferentially extending elastic member extending along a waist opening defined by longitudinally opposite edges of said front and rear waist regions, respectively, when the diaper is being worn by a wearer; and all of said spots are longitudinally spaced from said circumferentially extending elastic member.

30. The diaper of claim 29, wherein each of said imaginary lines intersects with at least one other of said imaginary lines.

31. The diaper of claim 29, wherein said elastic inner layer is distinct and separate from said circumferentially extending elastic member.

32. The diaper of claim 29, wherein said imaginary lines comprise a first set of non-intersecting imaginary lines which are generally disposed in a first direction, and a second set of non-intersecting imaginary lines which are generally disposed in a second direction crossing said first direction; and a spacing between adjacent said spots arranged on the same imaginary line is smaller than a spacing between adjacent said non-intersecting imaginary lines of the first or second set.

33. The diaper claim 29, wherein at least a portion of said front panel in the region that is coelevational with the upper end of the leg openings formed in the diaper is devoid of said circumferentially extending elastic member.

* * * * *